US00PP10323P

United States Patent [19]

Lamb et al.

[11] Patent Number: Plant 10,323

[45] Date of Patent: Apr. 7, 1998

[54] ANTHURIUM PLANT NAMED 'NORTHSTAR'

[75] Inventors: Ann E. Lamb, Sebring; Robert D. Hartman, Lake Placid, both of Fla.

[73] Assignee: Twyford International, Inc., Santa Paula, Calif.

[21] Appl. No.: 629,769

[22] Filed: Apr. 9, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

An Anthurium plant named 'Northstar' having heart shaped light pink spathes which fade to white, and a pink spadix, with the spathes being held well above the foliage in the center of the plant. The inflorescence has a light sweet, mint fragrance. The leaves are dark green, leathery, with a glossy surface, and are abundantly produced. The plant is moderately branched.

1 Drawing Sheet

The present invention comprises a new and distinct cultivar of Anthurium, botanically known as *Anthurium hybrid*, and referred to by the cultivar name 'Northstar'.

The new cultivar is a product of a breeding program carried out by the inventors Ann E. Lamb and Robert D. Hartman in Apopka and Sebring, Fla., and is the result of the following cross made in Sebring in February 1993:

Anthurium 'White Aristocrat', disclosed in U.S. Plant Pat. No. 8,821×An unnamed Anthurium hybrid identified by a proprietary code number.

The cultivar was discovered from the progeny of the stated cross in May 1995 by Ann E. Lamb. Tissue culture performed by or under the supervision of Ann E. Lamb at Sebring, Fla. was used to increase the number of plants for evaluation and has demonstrated the stability of the combination of characteristics of 'Northstar' from generation to generation.

The following observations, measurements and values describe plants grown in Homestead, Fla. under shade house conditions which closely approximate those generally used in horticulture practice.

The following traits have been repeatedly observed to be characteristics which in combination distinguish 'Northstar' from other Anthuriums of the same general type, for example, the patented cultivar 'White Aristocrat' to which comparative reference is made.

1. The plant produces very light pink spathes, which fade to white, with a contrasting pink spadix, with the spathes being carried well above the foliage in the center of the plant.

2. The flowers have a light, sweet mint fragrance when new.

3. The spathes are distinctly cupped and heart shaped, and do not reflex.

4. The leaves are medium to dark green, leathery and have a glossy surface.

5. The growth habit is moderately branched.

Compared to 'White Aristocrat', 'Northstar' produces light pink spathes which gradually change to white, with a contrasting pink spadix. The leaves of 'Northstar' are darker green, thicker, wider and more abundant than those of 'White Aristocrat'.

All color references are measured against The Royal Horticultural Society color chart. Colors are approximate as color depends on horticultural practices such as light level and fertilization rate, among others, without, however, any variance in genotype.

The color photographic drawing comprises a top perspective view of the inflorescence and foliage of a plant of 'Northstar' in a 20.3 cm pot approximately 12 months after planting a 20 week old liner obtained by tissue culture and grown under appropriate growing conditions. Colors are as accurate as possible with color illustrations of this type.

Origin: Seedling selected from a cross of Anthurium 'White Aristocrat'×an unnamed hybrid identified by a proprietary code number.

Classification: *Anthurium hybrid*, cv. 'Northstar'.

Propagation: Asexual propagation either by tissue culture or division.

Inflorescence

Immature: The spathe is tightly rolled around the spadix and emerges from the petiole sheath. The spathe is fully open about when the peduncle is fully elongated, approximately 36 cm to 42 cm above the soil surface. The color of the flower peduncle is 146 A-B, tinged with 165 A.

Mature:

*Color.*—Fully open: Upper surface: 49 C-D. Lower surface: 151 A, or lighter than, but closest to 49 D. Faded: Upper Surface: 155 D. Lower Surface: 155 D. The margin of the spathe at the junction of the spadix and spathe is often bordered with 178 B. The primary veins at the junction of the spathe and spadix are 144 A.

*Arrangement.*—The inflorescence terminates from a straight wiry peduncle and opens vertically above the leaves.

*Shape.*—The spathe is heart shaped with a cordate base and a cuspidate tip. It is distinctly cupped, and does not reflect with age.

*Size.*—The fully expanded spathe is approximately 6.0 cm to 6.9 cm long and approximately 5.0 cm to 5.7 cm in width.

*Flowering time.*—After approximately 12 months from a 20 week old liner for an untreated plant as illustrated in the photograph and depending on season, approximately 8 to 11 blossoms will be present. Smaller blooms may occur on less mature growth. First flowers are typically produced approximately 3–4 months after planting a 20 week old liner. Approximately 3 flowers are present.

Reproductive Organs:

*Spadix.*—Size: Approximately 3.8 cm to 4.2 cm in height and approximately 7.5 mm in width. Color: When the spathe unrolls, the spadix is 69 B, with 50 B at the tip. Stamens: Anthers and filaments are minute and not clearly visible. Pollen is white in color. Pistil: Translucent white, protruding between the stamens, firmly fixed to the main axil. The pistils extend approximately 0.2 mm beyond the stamens.

General appearance: Under appropriate growing conditions, 'Northstar' reaches a marketable size of approximately 25 cm to 28 cm in height and approximately 42 cm to 55 cm in width.

Leaves:

*Form.*—The leaf blade is ovate with an acuminate tip and a cordate to truncate base. The midrib is straight over the length of the leaf, and curved downward at the tip. The leaf margins are straight, or wavy. The leaf blade is leathery in texture, with a glossy surface.

*Size.*—Leaf blades of a mature size plant are approximately 18.0 cm to 20.4 cm in length and approximately 11.4 cm to 13.4 cm in width measured at the widest point.

*Veins.*—The veins are sunken. The leaf blade is flat or slightly convex between veins on the upper surface. The midrib protrudes from the upper surface of the leaf for approximately ⅔ the length of the leaf. Well defined primary veins radiate out from the juncture of the petiole and the leaf. Veins stand out prominently on the lower side. There are approximately 4–6 primary veins on the leaf.

*Petiole.*—The petiole is approximately 17.2 cm to 20.3 cm in height from the base of the petiole to the base of the leaf blade on the primary shoot. The petiole is approximately 4.0 mm in diameter just below the geniculum. The petiole below the geniculum is straight. Secondary shoots are somewhat smaller depending on the age of the shoot.

*Petiole wings.*—Petiole wings are approximately 2.5 cm in length and approximately 3.0 mm in width at their midpoint. The tip of the petiole wings is round. There is approximately 15 cm between the top of the wing and the base of the geniculum.

*Geniculum.*—The geniculum is approximately 2.2 cm to 2.5 cm in length, approximately 5.0 mm in diameter, and is often curved. There is no space between the top of the geniculum and the base of the leaf blade.

*Lobes.*—The leaf has two rounded lobes which do not extend past the petiole. The distance from the petiole/leaf juncture to the highest point on the lobes is approximately 5.8 cm to 6.9 cm.

*Colors.*—Upper surface: Much darker and greener than, but closest to 137 A. Lower surface: 146 B-C. Midrib, upper surface: 146 A-B, tinged with 165 A at the junction of the primary veins and midrib. Midrib, lower surface: 146 C-D. Petiole: 146 A, tinged with 165 A. The petioles darken with direct exposure to bright light. Petiole wing: 146 A. Geniculum: 146 C.

Roots: White fleshy roots with fine laterals.

I claim:

1. A new and distinct cultivar of Anthurium plant named 'Northstar' as illustrated and described.

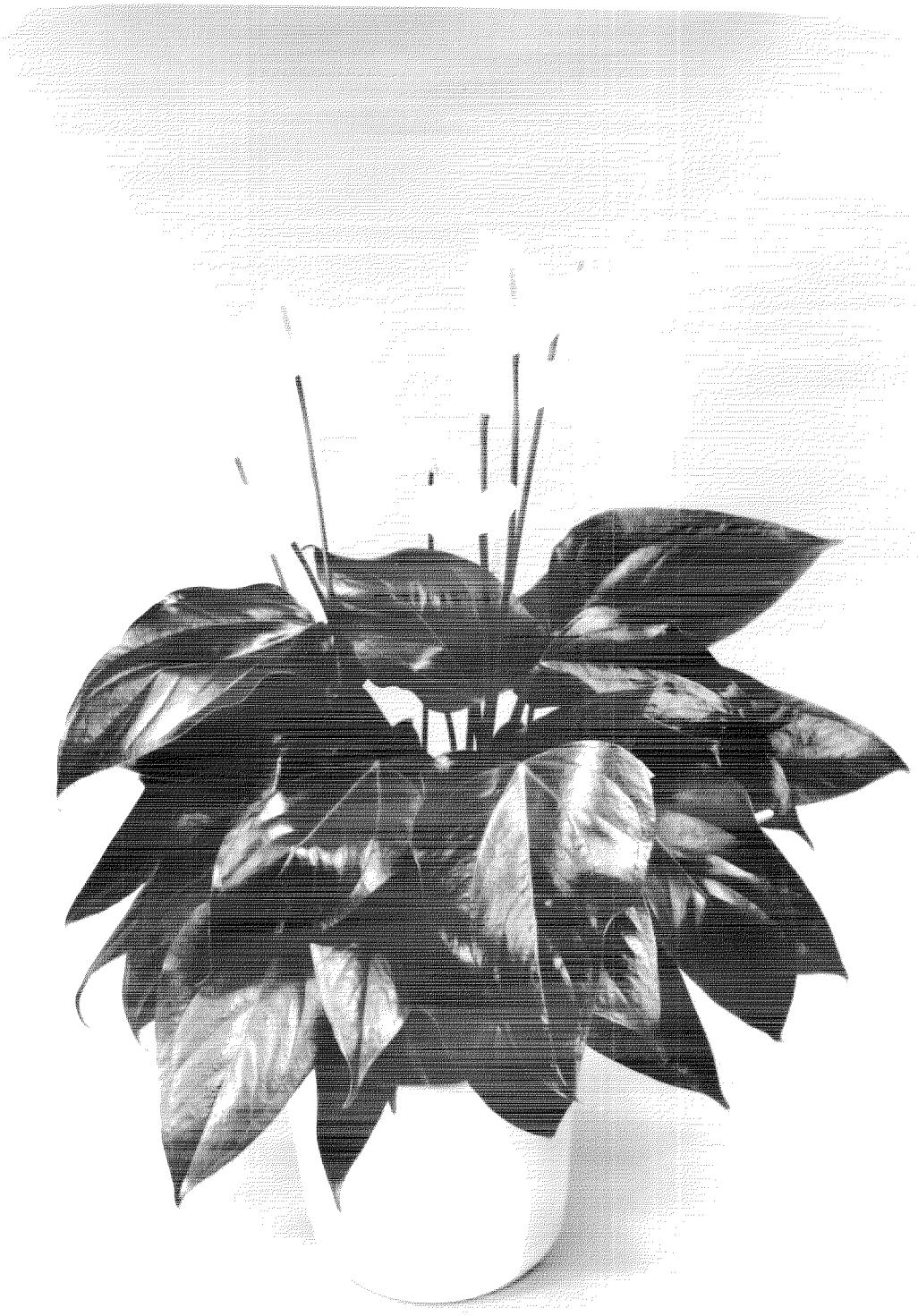

* * * * *